(12) United States Patent
Zhang et al.

(10) Patent No.: US 9,821,087 B2
(45) Date of Patent: Nov. 21, 2017

(54) BIO-ARTIFICIAL PERIOSTEUM BASED ON MICROPATTERNING OF BIOMIMETIC MINERALIZED CALCIUM-PHOSPHORUS NANOPARTICLES AND METHOD FOR MANUFACTURING THE SAME

(71) Applicant: HUAZHONG UNIVERSITY OF SCIENCE AND TECHNOLOGY, Wuhan (CN)

(72) Inventors: Shengmin Zhang, Wuhan (CN); Gaojie Yang, Wuhan (CN); Haoming Liu, Wuhan (CN); Yu Liu, Wuhan (CN)

(73) Assignee: HUAZHONG UNIVERSITY OF SCIENCE AND TECHNOLOGY, Wuhan (CN)

( * ) Notice: Subject to any disclaimer, the term of this patent is extended or adjusted under 35 U.S.C. 154(b) by 0 days.

(21) Appl. No.: 15/079,872

(22) Filed: Mar. 24, 2016

(65) Prior Publication Data

US 2017/0100508 A1 Apr. 13, 2017

(30) Foreign Application Priority Data

Oct. 9, 2015 (CN) .......................... 2015 1 0648173

(51) Int. Cl.
*A61L 27/54* (2006.01)
*A61L 27/24* (2006.01)
(Continued)

(52) U.S. Cl.
CPC .............. *A61L 27/24* (2013.01); *A61L 27/12* (2013.01); *A61L 27/365* (2013.01); *A61L 27/54* (2013.01);
(Continued)

(58) Field of Classification Search
CPC ..................................................... A61F 2/3076
See application file for complete search history.

(56) References Cited

FOREIGN PATENT DOCUMENTS

CN 101628130 A 1/2010
WO 9641595 A1 12/1996

OTHER PUBLICATIONS

Frohbergh et al, "Bone Tissue Engineering: Nanomedicine Approaches", Wiley Online Library, Reviews in Cell Bioloy and Mooecular Medicine, Jul. 27, 2015, Abstract.*

(Continued)

*Primary Examiner* — Carlos Azpuru
(74) *Attorney, Agent, or Firm* — Tim Tingkang Xia, Esq.; Locke Lord LLP

(57) ABSTRACT

The disclosure relates to a bio-artificial periosteum based on micropatterning of biomimetic mineralized calcium-phosphorus nanoparticles and a method for manufacturing the same. The method includes: first, a micropatterned biomimetic mineralized calcium-phosphorus nanoparticle layer is manufactured on a surface of an inert substrate; then, an organic polymer is cross-linked and solidified on the micropatterned biomimetic mineralized calcium-phosphorus nanoparticle layer; at last, the inert substrate is removed, so that the bio-artificial periosteum based on micropatterning of biomimetic mineralized calcium-phosphorus nanoparticles is obtained. The bio-artificial periosteum not only simulates the composition of natural bone in material components, but also realizes high degree of biomimesis in micro-nano size in structure. Moreover, the distribution of bone marrow mesenchymal stem cells can be regulated by the bio-artificial periosteum, so that the cells can be effectively defined on a surface of calcium-phosphorus particle micropattern and a high degree of ordered alignment thereof can be realized.

10 Claims, 2 Drawing Sheets

(51) Int. Cl.
*A61L 27/36* (2006.01)
*A61L 27/12* (2006.01)
*B28B 1/14* (2006.01)
*B28B 7/00* (2006.01)
*B28B 7/34* (2006.01)
*G03F 7/16* (2006.01)

(52) U.S. Cl.
CPC .............. *B28B 1/14* (2013.01); *B28B 7/0064* (2013.01); *B28B 7/342* (2013.01); *B28B 7/346* (2013.01); *B28B 7/348* (2013.01); *G03F 7/16* (2013.01); *A61L 2430/02* (2013.01)

(56) References Cited

OTHER PUBLICATIONS

Office Action issued by the State Intellectual Property Office of the Peoples Republic of China dated Aug. 2, 2017 for Application No. 201510648173.9.

Huang, Yong-Xia et al., "Electrochemical Construction and Biological Performance of Micropatterned CaP Films", Acta Physico-Chimica Sinica, vol. No. 26, Issue No. 8, pp. 2057-2060, 2010.

Sun, Rui et al., "In vitro constructing artificial biomimetic periosteum", Chinese Journal of Tissue Engineering Research, China Academic Journal Electronic Publishing House, vol. No. 17, Issue No. 42, pp. 7349-7355, Oct. 15, 2013.

Shi, Xuetao et al., "Enhanced Osteogenesis by a Biomimic Pseudo-Periosteum-Involved Tissue Engineering Strategy", Advanced Healthcare Materials, vol. No. 2, Issue No. 9, pp. 1229-1235, 2013.

Ma, Jun et al., "Biomimetic self-assembly of apatite hybrid materials: From a single molecular template to bi-/multi-molecular templates", JBA-06757—https://doi.org/10.1016/j.biotechadv.2013.10.014, Elsevier, Biotechnology Advances, vol. No. 32, Issue No. 4, pp. 744-760, Jul.-Aug. 2014.

\* cited by examiner

BIO-ARTIFICIAL PERIOSTEUM BASED ON MICROPATTERNING OF BIOMIMETIC MINERALIZED CALCIUM-PHOSPHORUS NANOPARTICLES AND METHOD FOR MANUFACTURING THE SAME

CROSS-REFERENCE TO RELATED APPLICATION

This application claims the priority to Chinese Patent Application No. 201510648173.9, filed on Oct. 9, 2015, in the State Intellectual Property Office of P.R. China, which is hereby incorporated herein in its entirety by reference.

FIELD OF THE INVENTION

The present disclosure relates to the technical field of biomedical material, and particularly to a bio-artificial periosteum based on micropatterning of biomimetic mineralized calcium-phosphorus nanoparticles and a method for manufacturing the same.

BACKGROUND OF THE INVENTION

Bone defect is a commonly seen intractable disease in clinical treatment. There are tens of thousands of patients every year who need bone repair treatment because they suffer from bone defect due to heredity, tumor, injury, infection or other reasons. With respect to the construct of bone tissue repair material, on the one hand, it should be guaranteed that the mechanical property of the bone tissue repair material matches that of natural bone tissue, and on the other hand, it should also be guaranteed that the tissue engineering material implanted in body can keep long term stability and can play the function of bone repair. Therefore, it is a new method and a development trend in bone defect repair to design new artificially synthesized material based on basic principles of regenerative medicine, tissue engineering, and micro-nano manufacturing, so as to play the functions of bone regeneration, repair, and reconstruction better, and perform better osteoinductivity and osteointegration ability.

Natural bone is a kind of multi-level biomineralized composite generated by deposition mediated by template protein molecules and then assembly of calcium-phosphorus minerals. Natural bone has a unique tissue structure and a perfect performance. In super micro-nano size, bones with two different forms, i.e., cancellous bone and compact bone, are both made of mineralized collagen that is arranged layer-by-layer in a parallel manner or arranged in concentric circles in a form of fiber bundle. In order to realize the matching of nano-material for bone repair and organism, not only the composition of the material should close to that of natural bone, but also the micro-nano structure of the material should simulate the layer-by-layer ordered arrangement of natural bone so as to realize high degree of biomimesis of implanted biomaterial. Therefore, it is a new strategy to construct nano bone material with biomimetic micropatterned ordered structure in bone tissue engineering research and clinical application, as well as a supplement for the case that the traditional research on nano-material for bone repair only aims at bone component simulation. Moreover, the patterning structure of the nano-material for bone repair realizes a breakthrough from two dimensional plane to three dimensional scaffold.

SUMMARY OF THE INVENTION

With respect to the technical defect in the prior art, the present disclosure provides a bio-artificial periosteum based on micropatterning of biomimetic mineralized calcium-phosphorus nanoparticles and a method for manufacturing the same.

In order to realize the aforesaid invention purpose, the present disclosure provides the following technical solution: a bio-artificial periosteum based on micropatterning of biomimetic mineralized calcium-phosphorus nanoparticles, comprising a micropatterned biomimetic mineralized calcium-phosphorus nanoparticle layer and an organic polymer that is cross-linked and solidified on the micropatterned biomimetic mineralized calcium-phosphorus nanoparticle layer.

According to the above solution, a micropattern is one selected from a group consisting of straight stripe, annular stripe, and mesh stripe.

According to the above solution, in addition to biomimetic mineralized calcium-phosphorus nanoparticles, raw material ingredients of the micropatterned biomimetic mineralized calcium-phosphorus nanoparticle layer further comprise macromolecules which would facilitate cell adhesion, bone growth factor, and/or anti-inflammatory drug.

According to the above solution, the organic polymer is one selected from a group consisting of collagen, gelatin, chitosan, hyaluronic acid, polylactic acid (PLA), polycaprolactone (PCL), polyglycolic acid (PGA), poly(lactic-co-glycolic acid) (PLGA), polyurethane (PU), and polycarbonate (PC).

The present disclosure further provides a method for manufacturing the bio-artificial periosteum based on micropatterning of biomimetic mineralized calcium-phosphorus nanoparticles, comprising the steps of:

(1) manufacturing a micropatterned biomimetic mineralized calcium-phosphorus nanoparticle layer, comprising the sub-steps of:

taking protein, polysaccharide, or synthetic molecule as a mineralization template, adding calcium-phosphorus salt to the mineralization template, and obtaining biomimetic mineralized calcium-phosphorus nanoparticles after codeposition and self-assembly in a biomimetic mineralization manner; dispersing the biomimetic mineralized calcium-phosphorus nanoparticles into water so as to prepare biomimetic mineralized calcium-phosphorus nanoparticle aqueous suspension; photoetching negative photoresist on a silicon wafer so as to prepare a micropattern array, forming a secondary seal through reversed moulding with PDMS adhesive, and forming a hydrophilic and soft agarose micropattern seal through reversed moulding with agarose; and dropwise adding or coating the biomimetic mineralized calcium-phosphorus nanoparticle aqueous suspension on a surface of the agarose micropattern seal so as to form a uniform thin layer, airing the layer to semidry, printing the layer on a surface of the inert substrate through a microcontact method, and removing agarose gel so as to obtain the micropatterned biomimetic mineralized calcium-phosphorus nanoparticle layer; or taking protein, polysaccharide, or synthetic molecule as a mineralization template, and dispersing the mineralization template into water so as to prepare mineralization template aqueous suspension; photoetching negative photoresist on a silicon wafer so as to prepare a micropattern array, forming a secondary seal through reversed moulding with PDMS adhesive, and forming a hydrophilic and soft agarose micropattern seal through reversed moulding with agarose; and dropwise adding or coating the mineralization template aqueous suspension on a surface of the agarose micropattern seal so as to form a uniform thin layer, airing the layer to semidry, printing the layer on a surface of the inert substrate through a micro-contact method, removing agarose gel so as to obtain a micropatterned mineralization template layer, and manufacturing biomimetic mineralized calcium-phosphorus nanoparticles on the mineralization template through codeposition in a biomimetic mineralization manner, so as to obtain the micropatterned biomimetic mineralized calcium-phosphorus nanoparticle layer; and (2) covering the micropatterned biomimetic mineralized calcium-phosphorus nanoparticle layer with a polymer solution, and removing the inert substrate after sufficient cross-linking and solidification so as to obtain the bio-artificial periosteum based on micropatterning of biomimetic mineralized calcium-phosphorus nanoparticles.

According to the above solution, the inert substrate is one selected from a group consisting of slide, silicon wafer, quartz plate, and polydimethylsiloxane (PDMS) adhesive.

According to the above solution, the protein serving as the mineralization template is one or more selected from a group consisting of collagen, bone morphogenetic protein, fibronectin, laminin, bone sialoprotein, silk fibroin, and serum protein; the polysaccharide serving as the mineralization template is one or more selected from a group consisting of glycosaminoglycan, proteoglycan, and chitosan; and the synthetic molecule serving as the mineralization template is one or more selected from a group consisting of synthetic amphoteric peptide molecules and synthetic amphoteric self-assembling molecules.

According to the above solution, the cross-linking and solidification in step (2) can be carried out through ultraviolet irradiation for 5 to 20 minutes or reaction at a temperature of 40° C. for 10 to 120 minutes after cross linker being added.

According to the above solution, the sub-step of obtaining biomimetic mineralized calcium-phosphorus nanoparticles after codeposition and self-assembly in a biomimetic mineralization manner in step (1) is specifically: adding a solution containing calcium ions to a mineralization template solution, mixing the solution uniformly, dropwise adding a solution containing phosphate ions, dropwise adding alkali solution simultaneously to adjust a pH value to a range between 7 and 8, stirring the solution in water bath with a temperature of 37° C. and aging it, suction filtrating or centrifugally cleaning obtained precipitation with ultra-pure water, lyophilizing and grinding so as to obtain biomimetic mineralized calcium-phosphorus nanoparticles.

According to the above solution, the sub-step of manufacturing biomimetic mineralized calcium-phosphorus nanoparticles on the micropatterned mineralization template through codeposition in a biomimetic mineralization manner, so as to obtain the micropatterned biomimetic mineralized calcium-phosphorus nanoparticle layer in step (1) is specifically: dropwise adding simulated body fluid or Dulbecco's Phosphate Buffered Saline (DPBS) containing calcium chloride on a surface of the micropatterned mineralization template layer, covering and immersing the layer in water bath with a temperature of 37° C. and aging it, and removing DPBS by washing with ultra-pure water after biomimetic mineralized calcium-phosphorus nanoparticles are deposited on the mineralization template in a biomimetic mineralization manner, so as to obtain the micropatterned biomimetic mineralized calcium-phosphorus nanoparticle layer.

The following beneficial effects can be brought about according to the present disclosure. (1) According to the present disclosure, the bio-artificial periosteum based on micropatterning of biomimetic mineralized calcium-phosphorus nanoparticles not only simulates the composition of natural bone in material components, but also realizes high degree of biomimesis in micro-nano size in structure. The bio-artificial periosteum simulates the self-assembling of mineralized bone collagen in nano size, and simulates the ordered structure of natural bone tissue material in micrometer size. Moreover, the distribution of bone marrow mesenchymal stem cells can be regulated by the bio-artificial periosteum, so that the cells can be effectively defined on a surface of calcium-phosphorus particle micropattern and a high degree of ordered alignment thereof can be realized. (2) The bio-artificial periosteum according to the present disclosure has a good histocompatibility, a low immunogenicity, a good degradability and an excellent mechanical property, as well as effective osteoconductivity and osteoinductivity. (3) The bio-artificial periosteum according to the present disclosure can be coated on bone fracture or bone defect area directly and applied to the treatment of bone nonunion. In addition, the bio-artificial periosteum can be rolled into a barrel shape and can be filled in the bone defect area directly. In a word, the bio-artificial periosteum according to the present disclosure has a good potential clinical application value.

DETAILED DESCRIPTION OF THE EMBODIMENTS

Figure 1:
FIG. 1 is a Transmission Electron Microscope (TEM) picture of biomimetic mineralized calcium-phosphorus nanoparticles.

The present disclosure will be further illustrated hereinafter with reference to the examples for a better understanding thereof. However, the present disclosure is not limited by the specific examples disclosed herein.

Example 1

A bio-artificial periosteum based on micropatterning of biomimetic mineralized calcium-phosphorus nanoparticles can be manufactured through the following method.

(1) Collagen solution (20 ml, 5 mg/ml) that is dissolved in acetic acid (0.5 M) is added to $Ca(NO_3)_2$ solution (200 ml, 0.05 M), $(NH_4)_2HPO_4$ solution (120 ml, 0.05 M) is dropwise added therein, and NaOH solution (1 M) is dropwise added therein at the same time to adjust a pH value of the solution to a range between 7 and 8. The above solution is stirred for two hours in water bath with a temperature of 37° C., and then aging for two days. The obtained precipitation is suction filtrated and cleaned with ultra-pure water, and then collagen-hydroxyapatite (COL-HA) powder, i.e., biomimetic mineralized calcium-phosphorus nanoparticles can be obtained after lyophilization and grinding.

(2) COL-HA (0.1 g) is added to ultra-pure water (2 ml), and COL-HA mineralized calcium-phosphorus nanoparticle aqueous suspension can be obtained after ultrasonic dispersion.

(3) Polydimethylsiloxane (PDMS) adhesive prepolymer is poured on a surface of a negative photoresist bottom die which has a groove-shaped micropattern with a width of 50 μm and a spacing of 30 μm, and then cross-linked and solidified for 12 hours in an oven with a temperature of 60° C. so as to obtain a secondary PDMS adhesive micropattern. Melted agarose (5 mg/ml) with a low melting point is poured on a surface of the above micropattern, and then the agarose is stripped after solidification at a temperature of 4° C. so as to obtain a tertiary agarose groove micropattern seal.

(4) COL-HA mineralized calcium-phosphorus nanoparticle aqueous suspension (0.1 ml) obtained in step (2) is dropwise added on a surface of the agarose micropattern seal obtained in step (3) in a uniform manner so as to form a thin layer, and the layer is aired to semidry. The aforesaid layer is printed on a smooth surface of the PDMS adhesive through a micro-contact method, put into water bath with a temperature of 40° C. for 15 minutes, and then took out for condensation. The agarose gel is removed, and then a biomimetic mineralized calcium-phosphorus nanoparticle layer with a straight stripe micropattern can be obtained.

(5) A solution with 1% glutaraldehyde and 2% gelatin is poured on a surface of the biomimetic mineralized calcium-phosphorus nanoparticle layer so as to cover the surface with a thickness of 1 to 2 mm. The layer is put in an oven with a temperature of 40° C. for cross-linking for 10 minutes, and then dried so as to form a film. The PDMS adhesive is removed, and then a bio-artificial periosteum based on biomimetic mineralized calcium-phosphorus nanoparticles micropattern with a straight stripe shape can be obtained.

Example 2

A bio-artificial periosteum based on micropatterning of biomimetic mineralized calcium-phosphorus nanoparticles can be manufactured through the following method.

(1) Silk fibroin solution (20 ml, 5 mg/ml) is added to CaCl$_2$ solution (200 ml, 0.05 M), Na$_2$HPO$_4$ solution (120 ml, 0.05 M) is dropwise added therein, and NaOH solution (1 M) is dropwise added therein at the same time to adjust a pH value of the solution to a range between 7 and 8. The above solution is stirred for one day in water bath with a temperature of 37° C. The obtained precipitation is suction filtrated and cleaned with ultra-pure water, and then silk fibroin-hydroxyapatite (SF-HA) powder, i.e., biomimetic mineralized calcium-phosphorus nanoparticles (as shown in FIG. 1) can be obtained after lyophilization and grinding.

(2) SF-HA (0.1 g) is added to ultra-pure water (2 ml) for ultrasonic dispersion, fibronectin (10 μg/ml) is added therein, and SF-HA biomimetic mineralized calcium-phosphorus nanoparticle aqueous suspension can be obtained.

(3) Polydimethylsiloxane (PDMS) adhesive prepolymer is poured on a surface of a negative photoresist bottom die which has a straight stripe groove-shaped micropattern with a width of 30 μm and a spacing of 50 μm, and then cross-linked and solidified for 12 hours in an oven with a temperature of 60° C. so as to obtain a secondary PDMS adhesive micropattern seal with a straight stripe groove shape. Melted agarose (5 mg/ml) with a low melting point is poured on a surface of the above micropattern, and then the agarose is stripped after solidification at a temperature of 4° C. so as to obtain a tertiary agarose micropattern seal with a straight stripe groove shape.

Figure 2:
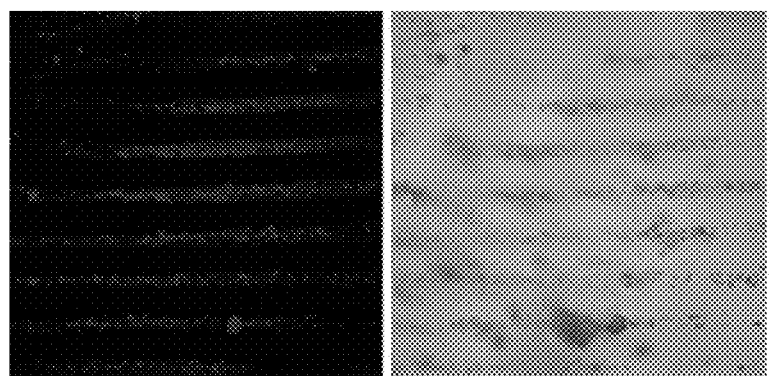
FIG. 2 shows a fluorescence image and a bright field image of biomimetic mineralized calcium-phosphorus nanoparticles which are regularly arranged on a surface of an inert substrate in a straight stripe shape.

(4) SF-HA aqueous suspension (0.1 ml) obtained in step (2) is dropwise added on a hydrophilic surface of a substrate, and is spread out in a uniform manner with a scraper. A surface of the agarose seal with the micropattern obtained in step (3) is covered on a surface of the aqueous suspension for 10 s in a uniform manner so as to form a thin layer, and the layer is aired to semidry. The aforesaid layer is printed on a smooth surface of the PDMS adhesive through a micro-contact method, put into water bath with a temperature of 40° C. for 15 minutes, and then took out for condensation. The agarose gel is removed, and then a biomimetic mineralized calcium-phosphorus nanoparticles with a straight stripe micropattern can be obtained. A fluorescence image and a bright field image of biomimetic mineralized calcium-phosphorus nanoparticles which are arranged on a surface of an inert substrate in a regular straight stripe shape are shown in FIG. 2.

Figure 3:
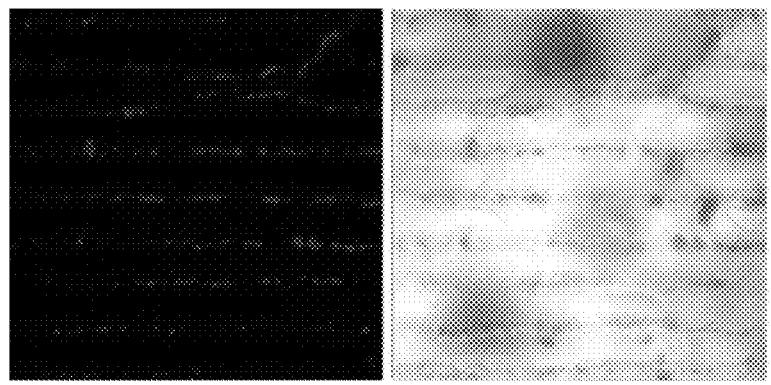
FIG. 3 shows a fluorescence image and a bright field image of a bio-artificial periosteum based on micropatterning of biomimetic mineralized calcium-phosphorus nanoparticles.
Figure 4:
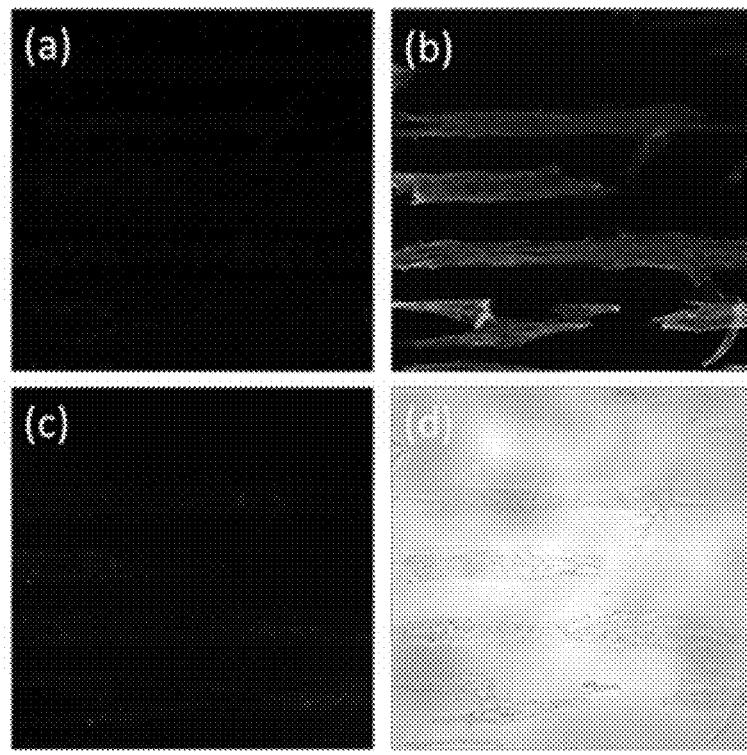
FIG. 4 shows fluorescence images when bone marrow mesenchymal stem cells grow on the bio-artificial periosteum based on micropatterning of biomimetic mineralized calcium-phosphorus nanoparticles according to the present disclosure and are aligned in a highly ordered manner, wherein (a) indicates cell nucleuses, (b) indicates cytoskeleton, (c) indicates nano bone particles, and (d) indicates a bright field image.

(5) Collagen solution (5 mg/ml) that is dissolved in acetic acid (0.1 M) is covered on a surface of the biomimetic mineralized calcium-phosphorus nanoparticle layer with a thickness of 1 to 2 mm, put in an oven with a temperature of 40° C. for drying, and then irradiated with an ultraviolet lamp for 5 to 10 minutes for cross-linking, so that a bio-artificial periosteum based on micropatterning of biomimetic mineralized calcium-phosphorus nanoparticles with a straight stripe shape can be obtained (as shown in FIG. 3). Bone marrow mesenchymal stem cells are planted on the obtained bio-artificial periosteum with the straight stripe micropattern. The product is fixed and colored after three days and can be observed through a fluorescence microscope (as shown in FIG. 4).

Example 3

A bio-artificial periosteum based on micropatterning of biomimetic mineralized calcium-phosphorus nanoparticles can be manufactured through the following method.

(1) Collagen solution (20 ml, 5 mg/ml) that is dissolved in acetic acid (0.5 M) is added to Ca(NO$_3$)$_2$ solution (200 ml, 0.05 M), (NH$_4$)$_2$HPO$_4$ solution (120 ml, 0.05 M) in which silk fibroin (0.1 g) is dissolved is dropwise added therein, and NaOH solution (1 M) is dropwise added therein at the same time to adjust a pH value of the solution to a range between 7 and 8. The above solution is stirred for two hours in water bath with a temperature of 37° C., and then aging for two days. The obtained precipitation is suction filtrated and cleaned with ultra-pure water, and then collagen-silk fibroin/hydroxyapatite (COL-SF/HA) powder, i.e., biomimetic mineralized calcium-phosphorus nanoparticles can be obtained after lyophilization and grinding.

(2) COL-SF/HA (0.1 g) is added to ultra-pure water (2 ml) for ultrasonic dispersion, polylysine (10 μg/ml) is added therein, and COL-SF/HA mineralized nanoparticle aqueous suspension can be obtained.

(3) Polydimethylsiloxane (PDMS) adhesive prepolymer is poured on a surface of a negative photoresist bottom die which has an annular-shaped micropattern with a width of 50 μm and a spacing of 30 μm, and then cross-linked and solidified for 12 hours in an oven with a temperature of 60°

C. so as to obtain a secondary PDMS adhesive micropattern. Melted agarose (5 mg/ml) with a low melting point is poured on a surface of the above micropattern, and then the agarose is stripped after solidification at a temperature of 4° C. so as to obtain a tertiary agarose annular groove micropattern seal.

(4) The aqueous suspension (0.1 ml) obtained in step (2) is dropwise added on a surface of the agarose micropattern seal obtained in step (3) in a uniform manner so as to form a thin layer, and the layer is aired to semidry. The aforesaid layer is printed on a smooth surface of the PDMS adhesive through a micro-contact method, put into water bath with a temperature of 40° C. for 15 minutes, and then took out for condensation. The agarose gel is removed, and then a biomimetic mineralized calcium-phosphorus nanoparticle layer with an annular stripe micropattern can be obtained.

Figure 5:
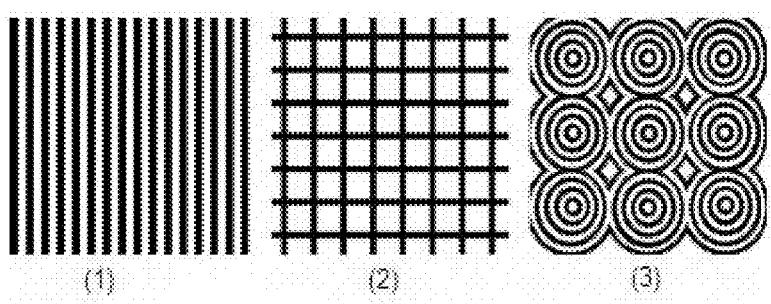
FIG. 5 shows biomimetic mineralized calcium-phosphorus nanoparticle micropatterns, wherein (1) shows a micropattern in a straight stripe shape, (2) shows a micropattern in a mesh stripe shape, and (3) shows a micropattern in an annular stripe shape.

(5) A solution with 2% gelatin is poured on a surface of the biomimetic mineralized calcium-phosphorus nanoparticle layer so as to cover the surface with a thickness of 1 to 2 mm, is put in an oven with a temperature of 40° C. for drying, and then irradiated with an ultraviolet lamp for 5 minutes for cross-linking. The PDMS adhesive is removed, and then a bio-artificial periosteum based on biomimetic mineralized calcium-phosphorus nanoparticles micropattern with an annular stripe shape can be obtained (as shown in FIG. 5).

Example 4

A bio-artificial periosteum based on micropatterning of biomimetic mineralized calcium-phosphorus nanoparticles can be manufactured through the following method.

(1) Collagen solution (20 ml, 5 mg/ml) that is dissolved in acetic acid (0.5 M) is added to $Ca(COOH)_2$ solution (200 ml, 0.05 M), $Na_2HPO_4$ solution (120 ml, 0.05 M) which contains sodium alginate (0.1 g) is dropwise added therein, and NaOH solution (1 M) is dropwise added therein at the same time to adjust a pH value of the solution to a range between 7 and 8. The above solution is stirred for two hours in water bath with a temperature of 37° C., and then aging for two days. The obtained precipitation is suction filtrated and cleaned with ultra-pure water, and then collagen fibroin-sodium alginate/hydroxyapatite(COL-SCA/HA) powder, i.e., biomimetic mineralized calcium-phosphorus nanoparticles can be obtained after lyophilization and grinding.

(2) COL-SCA/HA (0.1 g) is added to ultra-pure water (2 ml) for ultrasonic dispersion, arginine-glycine-aspartic acid polypeptide (10 μg/ml) is added therein, and COL-SCA/HA mineralized nanoparticle aqueous suspension can be obtained.

(3) Polydimethylsiloxane (PDMS) adhesive prepolymer is poured on a surface of a negative photoresist bottom die which has a "#"-shaped groove micropattern with a width of 50 μm and a spacing of 100 μm, and then cross-linked and solidified for 12 hours in an oven with a temperature of 60° C. so as to obtain a secondary PDMS adhesive micropattern. Melted agarose (5 mg/ml) with a low melting point is poured on a surface of the above micropattern, and then the agarose is stripped after solidification at a temperature of 4° C. so as to obtain a tertiary agarose mesh-shaped groove micropattern seal.

(4) The aqueous suspension (0.1 ml) obtained in step (2) is dropwise added on a surface of the agarose micropattern seal obtained in step (3) in a uniform manner so as to form a thin layer, and the layer is aired to semidry. The aforesaid layer is printed on a smooth surface of the PDMS adhesive through a micro-contact method, put into water bath with a temperature of 40° C. for 15 minutes, and then took out for condensation. The agarose gel is removed, and then a biomimetic mineralized calcium-phosphorus nanoparticle layer with a mesh stripe micropattern can be obtained.

(5) A solution with 2% gelatin and collagen (5 mg/ml), in which a cross linker, i.e., genipin (5%), is added, is poured on a surface of the biomimetic mineralized calcium-phosphorus nanoparticle layer so as to cover the surface with a thickness of 1 to 2 mm. The layer is put in an oven with a temperature of 40° C. for cross-linking for one hour, and then dried so as to form a film. The PDMS adhesive is removed, and then a bio-artificial periosteum based on biomimetic mineralized calcium-phosphorus nanoparticles micropattern with a mesh stripe shape can be obtained (as shown in FIG. 5).

Example 5

A bio-artificial periosteum based on micropatterning of biomimetic mineralized calcium-phosphorus nanoparticles can be manufactured through the following method.

(1) Polydimethylsiloxane (PDMS) adhesive prepolymer is poured on a surface of a negative photoresist bottom die which has a stripe groove-shaped micropattern with a width of 50 μm and a spacing of 30 μm, and then cross-linked and solidified for 12 hours in an oven with a temperature of 60° C. so as to obtain a secondary PDMS adhesive micropattern. Melted agarose (5 mg/ml) with a low melting point is poured on a surface of the above micropattern, and then the agarose is stripped after solidification at a temperature of 4° C. so as to obtain a tertiary agarose groove micropattern seal.

(2) Silk fibroin solution (5 mg/ml) is dropwise added on a smooth surface of a glass sheet, and is spread out on the surface in a uniform manner. The agarose seal with a micropattern surface is covered on the surface of the silk fibroin solution for 10 s, took out with a pair of tweezers and then aired to semidry. The product is printed on a smooth surface of the PDMS adhesive through a micro-contact method, put into water bath with a temperature of 40° C. for 15 minutes, and then took out for condensation. The agarose gel is removed, and then a template protein layer with a stripe-shaped micropattern can be obtained.

(3) The PDMS adhesive on which the micropatterned template protein layer is printed obtained in step (2) is put in a dish, and Dulbecco's Phosphate Buffered Saline (DPBS) (10 ml) which contains anhydrous calcium chloride (0.1 mg/ml) is added so as to completely cover the surface thereof. The dish is put into water bath with a temperature of 37° C. for two days, and salt ions residual on the surface are cleaned by ultra-pure water, so that a biomimetic mineralized calcium-phosphorus nanoparticle layer with a straight stripe micropattern can be obtained.

(4) A solution with 1% glutaraldehyde and 2% gelatin is poured on a surface of the micropatterned biomimetic mineralized calcium-phosphorus nanoparticle layer so as to cover the surface with a thickness of 1 to 2 mm. The layer is put in an oven with a temperature of 40° C. for cross-linking for 10 minutes, and then dried so as to form a film. The PDMS adhesive is removed, and then a bio-artificial periosteum based on biomimetic mineralized calcium-phosphorus nanoparticles micropattern with a straight stripe shape can be obtained.

Example 6

A bio-artificial periosteum based on micropatterning of biomimetic mineralized calcium-phosphorus nanoparticles can be manufactured through the following method.

(1) Polydimethylsiloxane (PDMS) adhesive prepolymer is poured on a surface of a negative photoresist bottom die which has a mesh-shaped groove micropattern with a width of 50 μm and a spacing of 100 μm, and then cross-linked and solidified for 12 hours in an oven with a temperature of 60° C. so as to obtain a secondary PDMS adhesive micropattern. Melted agarose (5 mg/ml) with a low melting point is poured on a surface of the above micropattern, and then the agarose is stripped after solidification at a temperature of 4° C. so as to obtain a tertiary agarose mesh-shaped groove micropattern seal.

(2) Type I collagen solution (5 mg/ml) that is prepared by acetic acid solution (0.5 M) is dropwise added on a surface of the agarose micropattern seal in a uniform manner and aired to semidry. The product is printed on a smooth surface of the PDMS adhesive through a micro-contact method, put into water bath with a temperature of 40° C. for 15 minutes, and then took out for condensation. The agarose gel is removed, and then a template protein layer with a mesh stripe micropattern can be obtained.

(3) The PDMS adhesive on which the micropatterned collagen is printed obtained in step (2) is put in a dish, and simulated body fluid (10 ml) which contains Bone Morphogenetic Protein-2 (BMP-2) (5 μg/ml) is added so as to completely cover the surface thereof. The dish is put into water bath with a temperature of 37° C. for two days, and salt ions residual on the surface are cleaned by ultra-pure water, so that a biomimetic mineralized calcium-phosphorus nanoparticle layer with a mesh stripe micropattern can be obtained.

(4) A solution with 1% glutaraldehyde and 2% gelatin is poured on a surface of the micropatterned biomimetic mineralized calcium-phosphorus nanoparticle layer so as to cover the surface with a thickness of 1 to 2 mm. The layer is put in an oven with a temperature of 40° C. for cross-linking for 10 minutes, and then dried so as to form a film. The PDMS adhesive is removed, and then a bio-artificial periosteum based on biomimetic mineralized calcium-phosphorus nanoparticles micropattern with a mesh stripe shape can be obtained.

It is obvious that, the above embodiments are described only for better understanding, rather than restricting, the present disclosure. Any person skilled in the art can make amendments or changes based on the contents disclosed herein. It is neither necessary nor feasible to enumerate all of the embodiments. Therefore, the amendments or changes that are readily conceivable based on the technical contents disclosed herein all fall into the protection scope of the present disclosure.

What is claimed is:

1. A bio-artificial periosteum based on micropatterning of biomimetic mineralized calcium-phosphorus nanoparticles, comprising a micropatterned biomimetic mineralized calcium-phosphorus nanoparticle layer and an organic polymer that is cross-linked and solidified on the micropatterned biomimetic mineralized calcium-phosphorus nanoparticle layer.

2. The bio-artificial periosteum according to claim 1, wherein a micropattern is one selected from a group consisting of straight stripe, annular stripe, and mesh stripe.

3. The bio-artificial periosteum according to claim 1, wherein in addition to biomimetic mineralized calcium-phosphorus nanoparticles, raw material ingredients of the micropatterned biomimetic mineralized calcium-phosphorus nanoparticle layer further comprise macromolecules which would facilitate cell adhesion, bone growth factor, and/or anti-inflammatory drug.

4. The bio-artificial periosteum according to claim 1, wherein the organic polymer is one selected from a group consisting of collagen, gelatin, chitosan, hyaluronic acid, polylactic acid, polycaprolactone, polyglycolic acid, poly (lactic-co-glycolic acid), polyurethane, and polycarbonate.

5. A method for manufacturing the bio-artificial periosteum based on micropatterning of biomimetic mineralized calcium-phosphorus nanoparticles according to any one of claims 1 to 4, comprising the steps of:

(1) manufacturing a micropatterned biomimetic mineralized calcium-phosphorus nanoparticle layer, comprising the sub-steps of:

taking protein, polysaccharide, or synthetic molecule as a mineralization template, adding calcium-phosphorus salt to the mineralization template, and obtaining biomimetic mineralized calcium-phosphorus nanoparticles after codeposition and self-assembly in a biomimetic mineralization manner; dispersing the biomimetic mineralized calcium-phosphorus nanoparticles into water so as to prepare biomimetic mineralized calcium-phosphorus nanoparticle aqueous suspension; photoetching negative photoresist on a silicon wafer so as to prepare a micropattern array, forming a secondary seal through reversed moulding with PDMS adhesive, and forming a hydrophilic and soft agarose micropattern seal through reversed moulding with agarose; and dropwise adding or coating the biomimetic mineralized calcium-phosphorus nanoparticle aqueous suspension on a surface of the agarose micropattern seal so as to form a uniform thin layer, airing the layer to semidry, printing the layer on a surface of the inert substrate through a micro-contact method, and removing agarose gel so as to obtain the micropatterned biomimetic mineralized calcium-phosphorus nanoparticle layer; or taking protein, polysaccharide, or synthetic molecule as a mineralization template, and dispersing the mineralization template into water so as to prepare mineralization template aqueous suspension; photoetching negative photoresist on a silicon wafer so as to prepare a micropattern array, forming a secondary seal through reversed moulding with PDMS adhesive, and forming a hydrophilic and soft agarose micropattern seal through reversed moulding with agarose; and dropwise adding or coating the mineralization template aqueous suspension on a surface of the agarose micropattern seal so as to form a uniform thin layer, airing the layer to semidry, printing the layer on a surface of the inert substrate through a micro-contact method, removing agarose gel so as to obtain a micropatterned mineralization template layer, and manufacturing biomimetic mineralized calcium-phosphorus nanoparticles on the mineralization template through codeposition in a biomimetic mineralization manner, so as to obtain the micropatterned biomimetic mineralized calcium-phosphorus nanoparticle layer; and (2) covering the micropatterned biomimetic mineralized calcium-phosphorus nanoparticle layer with a polymer solution, and removing the inert substrate after sufficient cross-linking and solidification so as to obtain the bio-artificial periosteum based on micropatterning of biomimetic mineralized calcium-phosphorus nanoparticles.

6. The method according to claim 5, wherein the inert substrate is one selected from a group consisting of slide, silicon wafer, quartz plate, and polydimethylsiloxane (PDMS) adhesive.

7. The method according to claim 5,
wherein the protein serving as the mineralization template is one or more selected from a group consisting of collagen, bone morphogenetic protein, fibronectin, laminin, bone sialoprotein, silk fibroin, and serum protein;
wherein the polysaccharide serving as the mineralization template is one or more selected from a group consisting of glycosaminoglycan, proteoglycan, and chitosan; and
wherein the synthetic molecule serving as the mineralization template is one or more selected from a group consisting of synthetic amphoteric peptide molecule and synthetic amphoteric self-assembling molecule.

8. The method according to claim 5, wherein the cross-linking and solidification in step (2) can be carried out through ultraviolet irradiation for 5 to 20 minutes or reaction at a temperature of 40° C. for 10 to 120 minutes after cross linker being added.

9. The method according to claim 5, wherein the sub-step of obtaining biomimetic mineralized calcium-phosphorus nanoparticles after codeposition and self-assembly in a biomimetic mineralization manner in step (1) is specifically: adding a solution containing calcium ions to a mineralization template solution, mixing the solution uniformly, dropwise adding a solution containing phosphate ions, dropwise adding alkali solution simultaneously to adjust a pH value to a range between 7 and 8, stirring the solution in water bath with a temperature of 37° C. and aging it, suction filtrating or centrifugally cleaning obtained precipitation with ultra-pure water, lyophilizing and grinding so as to obtain biomimetic mineralized calcium-phosphorus nanoparticles.

10. The method according to claim 5, wherein the sub-step of manufacturing biomimetic mineralized calcium-phosphorus nanoparticles on the micropatterned mineralization template through codeposition in a biomimetic mineralization manner, so as to obtain the micropatterned biomimetic mineralized calcium-phosphorus nanoparticle layer in step (1) is specifically: dropwise adding simulated body fluid or Dulbecco's Phosphate Buffered Saline (DPBS) containing calcium chloride on a surface of the micropatterned mineralization template layer, covering and immersing the layer in water bath with a temperature of 37° C. and aging it, and removing DPBS by washing with ultra-pure water after biomimetic mineralized calcium-phosphorus nanoparticles are deposited on the mineralization template in a biomimetic mineralization manner, so as to obtain the micropatterned biomimetic mineralized calcium-phosphorus nanoparticle layer.

\* \* \* \* \*